(12) United States Patent
Fujimura et al.

(10) Patent No.: US 11,668,708 B2
(45) Date of Patent: Jun. 6, 2023

(54) METHOD FOR REDUCING MEASUREMENT ERROR IN LATEX AGGLUTINATION IMMUNOASSAY

(71) Applicant: SEKISUI MEDICAL CO., LTD., Tokyo (JP)

(72) Inventors: Kengo Fujimura, Tokyo (JP); Junichi Kondou, Tokyo (JP); Mitsuaki Yamamoto, Tokyo (JP)

(73) Assignee: SEKISUI MEDICAL CO., LTD., Tokyo (JP)

( * ) Notice: Subject to any disclaimer, the term of this patent is extended or adjusted under 35 U.S.C. 154(b) by 11 days.

(21) Appl. No.: 16/651,872

(22) PCT Filed: Sep. 29, 2017

(86) PCT No.: PCT/JP2017/035479
§ 371 (c)(1),
(2) Date: Mar. 27, 2020

(87) PCT Pub. No.: WO2019/064491
PCT Pub. Date: Apr. 4, 2019

(65) Prior Publication Data
US 2020/0232977 A1    Jul. 23, 2020

(51) Int. Cl.
*G01N 33/53* (2006.01)
*G01N 33/543* (2006.01)

(52) U.S. Cl.
CPC ....... *G01N 33/543* (2013.01); *G01N 2458/00* (2013.01)

(58) Field of Classification Search
None
See application file for complete search history.

(56) References Cited

U.S. PATENT DOCUMENTS

| | | | | |
|---|---|---|---|---|
| 3,309,275 A * | 3/1967 | Treacy | ........ | G01N 33/76 436/524 |
| 3,551,555 A | 12/1970 | Schuurs | | |
| 4,600,698 A * | 7/1986 | Toth | ........ | G01N 33/543 13 436/534 |
| 4,988,630 A * | 1/1991 | Chen | ........ | G01N 21/253 422/73 |
| 5,055,395 A | 10/1991 | Toth | | |
| 2016/0264671 A1 * | 9/2016 | Kufer | ........ | C07K 16/2809 |

FOREIGN PATENT DOCUMENTS

| | | |
|---|---|---|
| CN | 104316694 A | 1/2015 |
| CN | 107137589 A | 9/2017 |
| EP | 2 098 864 A1 | 9/2009 |
| JP | 10-213582 A | 8/1998 |
| JP | 10-239317 A | 9/1998 |
| JP | 2006-71754 A | 3/2006 |
| JP | 2013-200208 A | 10/2013 |
| JP | 2016-31250 A | 3/2016 |
| JP | 2017-134067 A | 8/2017 |
| JP | 2017-181377 A | 10/2017 |

OTHER PUBLICATIONS

Melamies et al., Evaluation of a Quantitative Photometric Latex Agglutination Immunoassy for a-Foetoprotein, J Clin. Chem. Clin. Biochem. vol. 25, 1987, pp. 173-176. (Year: 1987).*
Nikolac, Nora., Lipemia: causes, interference mechanisms, detection and management, Biochemia Medica 2014; 24(1), pp. 57-67. (Year: 2014).*
Extended European Search Report for European Application No. 17927217.4, dated Mar. 29, 2021.
Indian Office Action for Indian Application No. 202047013419, dated Aug. 3, 2021, with English translation.
Korean Office Action for Korean Application No. 10-2020-7012027, dated Sep. 13, 2021, with English translation.
English translation of International Preliminary Report on Patentability and Written Opinion dated Apr. 9, 2020, in PCT/JP2017/035479 (Forms PCT/IB/338, PCT/IB/373, and PCT/ISA/237).
International Search Report dated Jan. 9, 2018, in PCT/JP2017/035479.
European Communication pursuant to Article 94(3) EPC for European Application No. 17927217.4, dated Dec. 8, 2021.
European Communication pursuant to Article 94(3) EPC for European Application No. 17927217.4, dated Mar. 21, 2022.
Chinese Office Action for Chinese Application No. 201780095469.X, dated Mar. 1, 2023, with English translation.

* cited by examiner

*Primary Examiner* — Gary Counts
(74) *Attorney, Agent, or Firm* — Birch, Stewart, Kolasch & Birch, LLP

(57) ABSTRACT

A method for avoiding the influence of a blood sample on a measurement error in a latex agglutination immunoassay. The measurement error caused by a blood sample in a latex agglutination immunoassay can be reduced by a method which includes a step of bringing the sample into contact, in a liquid phase, with latex particles carrying a substance having a specific affinity for an analyte in the presence of imidazole.

13 Claims, No Drawings

METHOD FOR REDUCING MEASUREMENT ERROR IN LATEX AGGLUTINATION IMMUNOASSAY

TECHNICAL FIELD

The present invention relates to a method for reducing a measurement error caused by a sample in a latex agglutination immunoassay using latex particles carrying a substance having a specific affinity for an analyte. In particular, the present invention relates to a method for reducing a measurement error caused by a blood sample, the method including a step of carrying out a latex immunoagglutination reaction in the presence of imidazole.

BACKGROUND ART

Latex agglutination immunoassay (also called latex turbidimetric immunoassay, and hereinafter sometimes referred to as LTIA) is frequently used as a measuring method for an analyte in a biological sample in the field of clinical examination. LTIA is a measuring method which uses, for example, latex particles carrying an antibody against an analyte, and detects, e.g. with an optical means, the degree of agglutination (turbidity) of the latex particles caused by binding between an antigen, which is the analyte, and the antibody-carrying latex particles.

Because of the use of a biological sample as a measurement target, there is a problem of measurement errors due to the influence of various interfering substances contained in the sample. In particular, since fat components are contained in a blood sample from a patient receiving an intravenous lipid emulsion or a patient with hyperlipidemia, a measurement error is produced by the influence of the fat component.

Known techniques for avoiding the influence of a fat component in a method for measuring a component of a blood sample using insoluble carrier particles include those disclosed in Patent Documents 1 to 3.

Patent Document 1 discloses a method which involves carrying out an antigen-antibody reaction in the presence of albumin, an enzyme having lipase activity, and a non-ionic surfactant in order to avoid the influence of chyle in a test sample such as serum or plasma. According to this method, the fat in the sample is structurally changed by the surfactant, and a core portion of the fat is degraded by lipase into fatty acids which, in turn, are adsorbed onto albumin. This avoids the interfering action of chyle on the antigen-antibody reaction.

Patent Document 2 discloses a method which, in the measurement of testosterone and estradiol using magnetic particles, eliminates an error, which is caused by the presence of lipid in a serum sample, by adding lipase to the sample.

However, it is necessary in such methods of Patent Documents 1 and Patent Document 2 to stably maintain the lipase activity in a constituent reagent because both methods involve degradation by lipase of lipids which are present in a sample and cause a measurement error.

Patent Document 3 discloses a method which utilizes a polynuclear phenol ethoxylate together with a secondary linear alcohol ethoxylate as a non-ionic surfactant in order to remove turbidity which is caused by lipid components of a blood sample such as serum or plasma. However, the document only describes the removal of turbidity caused by a fat component of the sample, and there is no specific description of an agglutination immunoassay using insoluble carrier particles such as latex particles.

CITATION LIST

Patent Literature

Patent Document 1: JP-A-2006-71754
Patent Document 2: JP-A-2013-200208
Patent Document 3: JP-A-H10-213582

SUMMARY OF INVENTION

Technical Problem

It is an object of the present invention to avoid the influence of a blood sample on a measurement error in a latex agglutination immunoassay.

Solution to Problem

The present inventors have made various studies to avoid the influence of a blood sample on a measurement error in a latex agglutination immunoassay and, as a result, have unexpectedly found that the influence of a blood sample on a measurement error can be avoided by varying buffer compositions in the liquid phase in which the sample is brought into contact with latex particles carrying the substance having a specific affinity for the analyte. The present invention has been completed based on this finding.

Thus, the present invention has the following features:

<1>
A method for reducing a measurement error caused by a blood sample in a latex agglutination immunoassay, comprising a step of bringing the sample into contact, in a liquid phase, with latex particles carrying a substance having a specific affinity for an analyte in the presence of imidazole or an imidazole derivative, or a salt thereof.

<2>
The method according to <1>, wherein the blood sample is serum or plasma.

<3>
The method according to <1> or <2>, wherein the concentration of imidazole or an imidazole derivative, or a salt thereof upon measurement of an agglutination reaction is not less than 37.5 mM and not more than 375 mM.

<4>
The method according to any one of <1> to <3>, wherein the latex agglutination immunoassay is based on a homogeneous method.

<5>
A method for measuring an analyte in a blood sample by a latex agglutination immunoassay, comprising a step of bringing the sample into contact, in a liquid phase, with latex particles carrying a substance having a specific affinity for the analyte in the presence of imidazole or an imidazole derivative, or a salt thereof.

<6>
The method according to <5>, wherein the blood sample is serum or plasma.

<7>
The method according to <5> or <6>, wherein the concentration of imidazole or an imidazole derivative, or a salt thereof upon measurement of an agglutination reaction is not less than 37.5 mM and not more than 375 mM.

<8>

The method according to any one of <5> to <7>, wherein the latex agglutination immunoassay is based on a homogeneous method.

<9>

A method for measuring an analyte in a blood sample by a latex agglutination immunoassay, comprising the following steps:

(1) bringing the sample into contact with imidazole or an imidazole derivative, or a salt thereof in a liquid phase;

(2) adding latex particles carrying a substance having a specific affinity for the analyte to the liquid phase after the step (1); and (3) measuring an agglutination reaction between the analyte and the latex particles after the step (2).

<10>

The method according to <9>, wherein the blood sample is serum or plasma.

<11>

The method according to <9> or <10>, wherein the concentration of imidazole or an imidazole derivative, or a salt thereof in the step (3) of measuring the agglutination reaction of the latex particles is not less than 37.5 mM and not more than 375 mM.

<12>

The method according to any one of <9> to <11>, wherein the latex agglutination immunoassay is based on a homogeneous method.

<13>

A reagent kit for measuring an analyte in a blood sample by a latex agglutination immunoassay, the kit comprising:

(1) a first reagent containing a buffer solution containing imidazole or an imidazole derivative, or a salt thereof; and (2) a second reagent containing latex particles carrying a substance having a specific affinity for the analyte.

<14>

The reagent kit according to <13>, wherein imidazole or an imidazole derivative, or a salt thereof is contained in such an amount as to be capable of adjusting the concentration of imidazole or an imidazole derivative, or a salt thereof to be not less than 37.5 mM and not more than 375 mM when measuring the analyte in the blood sample by the latex agglutination immunoassay.

<15>

The reagent kit according to <13> or <14>, wherein the latex agglutination immunoassay is based on a homogeneous method.

<16>

A liquid reagent for measuring an analyte in a blood sample by a latex agglutination immunoassay, comprising imidazole or an imidazole derivative, or a salt thereof.

<17>

The liquid reagent according to <16>, wherein imidazole or an imidazole derivative, or a salt thereof is contained in such an amount as to be capable of adjusting the concentration of imidazole or an imidazole derivative, or a salt thereof to be not less than 37.5 mM and not more than 375 mM when measuring the analyte in the blood sample by the latex agglutination immunoassay.

<18>

The liquid reagent according to <16> or <17>, wherein the latex agglutination immunoassay is based on a homogeneous method.

<19>

An agent for reducing a measurement error caused by a blood sample in a latex agglutination immunoassay, comprising imidazole or an imidazole derivative, or a salt thereof as an active ingredient.

Advantageous Effects of Invention

According to the present invention, by reducing a measurement error caused by a blood sample in a latex agglutination immunoassay, it is now possible to perform accurate measurement.

DESCRIPTION OF EMBODIMENTS (Latex Agglutination Immunoassay)

LTIA (latex agglutination immunoassay) is a method for measuring an analyte such as an antigen or an antibody by employing latex particles carrying an immobilized substance having a specific affinity for the analyte, and is widely used in the field of clinical examination. The LTIA method for measuring an antigen as an analyte is roughly classified into: a method which comprises reacting an antigen as an analyte with latex particles carrying an immobilized antibody against the antigen to form a sandwich-type immune complex, and measuring the analyte (antigen) based on the degree of agglutination of the latex particles due to the formation of the immune complex; and a method which comprises allowing antigen-immobilized latex particles to compete with an antigen (analyte) in the sample inhibiting the formation of an immune complex of the latex particles and an antibody, and measuring the analyte (antigen) from the degree of the inhibition of agglutination of the latex particles associated with the inhibition of the formation of the immune complex.

(Sample)

A sample for use in the present invention is a blood sample such as whole blood, serum or plasma.

(Reduction in Measurement Error)

In LTIA, due to some component of a blood sample, latex particles carrying an immobilized substance having a specific affinity for an analyte often undergo agglutination which should not occur (positive measurement error), or often fail to undergo agglutination which should occur (negative measurement error). Such phenomena are called nonspecific reaction, and are known to cause various measurement errors.

As used herein, "reducing a measurement error" refers to approximation of a measurement value with the aforementioned positive or negative measurement error to an intrinsic measurement value (true value).

As used herein, "a measurement error caused by a blood sample" refers to a measurement error produced by nonspecific reaction caused by a component(s) of the blood sample. The component(s) of the blood sample which causes nonspecific reaction may include lipids such as chyle, simple lipids or triglycerides.

The present invention is directed to a reduction of a measurement error produced especially in a blood sample from an individual with chyle characteristics (individual in a high-fat state) or an individual who has received a fat emulsion intravenously.

(Fat Emulsion)

The fat emulsion may be an oil-in-water fat emulsion prepared by emulsifying an oil or fat with an emulsifier into fat particles having an average particle diameter of not more than 1 μm, preferably not more than 0.5 μm, more preferably not more than 0.3 µm. Various fat emulsions which are used for transfusion (intravenous injection) can be used. Examples of commercial products include Intralipos (registered trademark, Otsuka Pharmaceutical Factory, Inc.), Intrafat (registered trademark, Nihon Pharmaceutical Co., Ltd.), and Intralipid (registered trademark, Fresenius Kabi Japan). The components of each product, described in a package insert, are purified soybean oil, purified egg-yolk lecithin, concentrated glycerin, sodium hydroxide (pH adjuster), etc.

The fat emulsion can be prepared by adding an oil or fat to a solution of an emulsifier dispersed in water, followed by stirring of the mixture to prepare a coarse emulsion, and then emulsifying the coarse emulsion by a common method such as a high-pressure emulsification method. In the case of using a high-pressure emulsification method, the emulsification may be performed, for example, by using an emulsifying machine such as a Manton Gaulin homogenizer, and allowing the coarse emulsion to pass through the emulsifying machine about 5 to 50 times under the condition of about 20 to 700 Kg/cm$^2$. To obtain a stable and fine-particle emulsion, the emulsification is preferably carried out in the presence of glucose and/or glycerin. This method can easily prepare an emulsion having an average particle diameter of not more than 0.17 µm. An auxiliary emulsifier may be used as necessary in carrying out the emulsification.

Any edible oil or fat can be used as the aforementioned oil or fat. Examples of preferable oils and fats may include vegetable oils (e.g. soybean oil, cottonseed oil, safflower oil, corn oil, coconut oil, labiate oil, and perilla oil), fish oils (e.g. cod liver oil), and chemically defined triglycerides such as medium-chain triglycerides [e.g. Panacet (trade name) and ODO (trade name)] and chemically synthesized triglycerides [e.g. 2-linoleoyl-1,3-dioctanoyl glycerol (8L8) and 2-linoleoyl-1,3-didecanoyl glycerol (10L10)]. These oils and fats may be used singly or in a combination of two or more. Any pharmaceutically usable emulsifying agent can be used as the aforementioned emulsifying agent. Specific examples of preferable emulsifying agents include egg-yolk phospholipid, hydrogenated egg-yolk phospholipid, soybean phospholipid, hydrogenated soybean phospholipid, and nonionic surfactants [e.g. Pluronic F68 and HCO-60 (trade names)]. Such emulsifiers may be used singly or in a combination of two or more.

Particularly preferably, soybean oil is used as the oil or fat and egg-yolk phospholipid is used as the emulsifier to prepare a fat emulsion in which the average particle diameter of fat particles is adjusted to not more than 0.3 µm, more preferably not more than 0.17 µm. While there is no particular limitation on the composition of the fat emulsion, an exemplary preferable fat emulsion contains an oil or fat in an amount of about 0.1 to 30 w/v %, preferably about 1 to 20 w/v %, more preferably about 2 to 10 w/v %, an emulsifier in an amount of about 0.01 to 10 w/v %, preferably about 0.05 to 5 w/v %, more preferably about 0.1 to 1 w/v %, and an appropriate amount of water.

The fat emulsion may also contain a sugar such as a reducing sugar. Examples of the reducing sugar include glucose, sucrose, and maltose. Such reducing sugars may be used as a mixture of two or more. It is also possible to use a mixture of such a reducing sugar with sorbitol, xylitol, and/or glycerin. The addition of such sugar(s) may be performed after or during the preparation of the emulsion. An exemplary preferable fat emulsion containing sugar contains an oil or fat in an amount of about 0.1 to 30 w/v %, preferably about 1 to 20 w/v %, more preferably about 2 to 10 w/v %, an emulsifier in an amount of about 0.01 to 10 w/v %, preferably about 0.05 to 5 w/v %, more preferably about 0.1 to 1 w/v %, sugar in an amount of about 1 to 60 w/v %, preferably about 5 to 40 w/v %, more preferably about 10 to 30 w/v %, and an appropriate amount of water.

The fat emulsion may also contain an anti-coloring agent (e.g. thioglycerol or dithiothreitol) for preventing coloring of the fat emulsion during sterilization and storage, and/or a buffering agent [e.g. L-histidine or tris(hydroxymethyl)aminomethane] for stabilizing the pH of the emulsion. The anti-coloring agent and the buffer may each be used generally in an amount of not more than about 1%. In the present invention, the fat emulsion may further contain a vitamin(s) (e.g. vitamin A, B vitamins, vitamin C, D vitamins, E vitamins, and K vitamins). These additives may be added during or after the preparation of the emulsion.

(Measuring Method)

The LTIA measuring method can measure an analyte by optically or electrochemically observing the degree of agglutination of latex particles. The optical observation may be performed by a method which measures the intensity of scattered light, the absorbance, or the intensity of transmitted light by means of an optical apparatus (an end point method, a rate method, or the like). An absorbance measurement value obtained by measurement of a sample is compared, for example, with an absorbance measurement value obtained by measurement of a standard substance (sample(s) containing a known concentration(s) of analyte), thereby calculating the concentration (quantitative value) of an analyte contained in the sample. The measurement of the absorbance of transmitted light or scattered light, or the like may be either a single-wavelength measurement or a two-wavelength measurement (difference or ratio between values at two wavelengths). The measurement wavelength(s) is generally selected from 500 nm to 800 nm.

The measurement of an analyte in a sample according to the present invention may be performed either manually or by using an apparatus such as a measuring apparatus. The measuring apparatus may be either a general-purpose automated analyzer or a dedicated measuring apparatus (dedicated machine). The measurement is preferably carried out by a process that includes a plurality of operation steps, such as a two-step process (two-reagent process).

(Analyte)

No particular limitation is placed on an analyte to be measured in the present invention as long as the substance can be measured by immunoassay method. Examples may include a variety of substances such as a protein (an antigen, a hapten, an antibody), a carbohydrate, a lipid, a nucleic acid, and a chemical substance (a hormone, a drug). Among these, an antigen, in particular a protein antigen, is preferable as an analyte. Specific examples may include, and are not limited to, soluble IL-2 receptor (sIL-2R), CRP, fibrin and fibrinogen degradation products, D-dimer, soluble fibrin (SF), lipoprotein(a) (Lp(a)), matrix metalloprotease-3 (MMP-3), prostate-specific antigen (PSA), IgG, IgA, IgM, IgE, IgD, anti-streptolysin O, rheumatoid factors, transferrin, haptoglobin, α1-antitrypsin, α1-acid glycoprotein, α2-macroglobulin, hemopexin, antithrombin-III, α-fetoprotein, CEA (carcinoembryonic antigen), ferritin, HBs-Ag (hepatitis B surface antigen), Anti-HBs (anti-hepatitis B surface antigen), HBe-Ag (hepatitis B e antigen), Anti-HBe (antibody to hepatitis B e antigen), and Anti-HBc (antibody to hepatitis B core antigen).

(Substance Having a Specific Affinity)

In the present invention, a substance having a specific affinity for an analyte, carried on latex particles, may be exemplified by a protein, a peptide, an amino acid, a lipid, a carbohydrate, a nucleic acid or a hapten. While there is no particular limitation on the molecular weight, the origin (natural or synthesized), etc. of the carried substance, it may be an antibody or an antigen which is usable in the immunoassay method that utilizes an immunoreaction.

(Antibody)

An antibody for use in the present invention may be either a polyclonal antibody or a monoclonal antibody, and preferably is a monoclonal antibody. Besides a whole antibody molecule, a functional fragment of an antibody, having an antigen-antibody reaction activity, can also be used as an antibody of the present invention. Besides an antibody obtained through an immunization process performed on a common animal (mouse, goat, sheep, etc.), it is also possible to use an antibody (chimeric antibody, humanized antibody, fully humanized antibody, etc.) obtained by changing the amino-acid sequence to that of an animal species which differs from an animal that is immunized with an immunogen (analyte), e.g. by a gene recombination technique. The functional fragment of an antibody may be, for example, $F(ab')_2$ or Fab', which is a fragment having an antigen-antibody reaction activity, or a single-chain antibody (scFv). Such a functional fragment of an antibody can be produced by treating an antibody, obtained in the aforementioned manner, with a proteolytic enzyme (e.g. pepsin or papain).

(Latex Particles)

There is no particular limitation on latex particles for use in the present invention as long as the latex particles are those which are commonly used as an immunoassay reagent. The latex particles can be obtained by polymerizing or copolymerizing a various kinds of monomer(s). Examples of usable monomers include: polymerizable unsaturated aromatic compounds including polymerizable monomers having a phenyl group, such as styrene, α-methyl styrene, o-methyl styrene, p-methyl styrene, p-chlorostyrene, 4-vinylbenzoate, divinylbenzene and vinyl toluene, polymerizable monomers having a phenyl group and a sulfonate, such as styrene sulfonate, divinylbenzene sulfonate, o-methyl styrene sulfonate and p-methyl styrene sulfonate, and polymerizable monomers having a naphthyl group, such as 1-vinylnaphthalene, 2-vinylnaphthalene, α-naphthyl (meth) acrylate and β-naphthyl (meth)acrylate; polymerizable unsaturated carboxylic acids such as (meth)acrylic acid, itaconic acid, maleic acid and fumaric acid; polymerizable unsaturated carboxylic acid esters such as methyl (meth) acrylate, ethyl (meth)acrylate, n-butyl (meth)acrylate, 2-hydroxyethyl (meth)acrylate, glycidyl (meth)acrylate, ethylene glycol-di-(meth)acrylate and tribromophenyl (meth)acrylate; and unsaturated carboxylic acid amides, polymerizable unsaturated nitriles, vinyl halides, and conjugated dienes, such as (meth)acrylonitrile, (meth)acrolein, (meth)acrylamide, N-methylol-(meth)acrylamide, methylenebis(meth) acrylamide, butadiene, isoprene, vinyl acetate, vinylpyridine, N-vinyl pyrrolidone, vinyl chloride, vinylidene chloride and vinyl bromide. These monomers may be appropriately selected depending on the surface characteristics, the specific gravity, etc. required, and can be used singly or as a mixture of two or more.

The average particle diameter of the latex particles is preferably 0.02 μm to 1.6 μm, more preferably 0.1 μm to 0.4 μm in view of the concentration of an analyte in a sample, the detection sensitivity of a measuring instrument, etc. In order to achieve a desired performance such as an improved sensitivity, the material and the particle size of the latex particles used can be appropriately selected. Alternatively, different types of latex particles, which differ in the material or in the particle size, can be used in combination. There is no particular limitation on the concentration of the latex particles upon measurement of an agglutination reaction according to the present invention; the concentration can be set appropriately depending on the intended sensitivity or performance.

(Latex Particles Carrying a Substance Having a Specific Affinity)

A substance having a specific affinity for an analyte can be immobilized and carried on latex particles by a known method such as a physical adsorption (hydrophobic bonding) method, a chemical bonding method, or a combination thereof.

The physical adsorption method can be carried out in a known manner: a substance having a specific affinity for an analyte and latex particles are mixed and brought into contact with each other in a solution such as a buffer solution, or a substance having a specific affinity for an analyte, dissolved in a buffer solution, is brought into contact with carrier latex particles.

The chemical bonding method can be carried out in a known manner as described, for example, in Clinical Pathology, Extra Issue, Special Edition No. 53 *"Immunoassay for Clinical Examination—Technology and Application—"*, edited by Japanese Society of Laboratory Medicine, issued in 1983 by Clinical Pathology Publication Society, or *"New Biochemistry Experiment Course 1, Protein IV"*, edited by Japanese Biochemical Society, issued in 1991 by Tokyo Kagaku Dojin. Specifically, the chemical bonding method can be carried out, for example, by mixing and contacting a substance having a specific affinity for an analyte and a carrier with a divalent crosslinking reagent such as glutaraldehyde, carbodiimide, an imide ester, or maleimide so as to react the divalent crosslinking reagent with an amino group, a carboxyl group, a thiol group, an aldehyde group, a hydroxyl group, or the like, in each of the substance having a specific affinity for an analyte and the carrier.

The substance having a specific affinity for an analyte, carried on latex particles, is preferably composed of a plurality of types in order to form a sandwich structure. For example, when the substance having a specific affinity is a monoclonal antibody, the monoclonal antibody may be composed of a plurality of types with different recognition sites. When the substance having a specific affinity is a polyclonal antibody, the polyclonal antibody may be derived from a single type of antiserum or a plurality of types of antiserum. Further, a monoclonal antibody and a polyclonal antibody may be used in combination.

In order to inhibit spontaneous agglutination, nonspecific reaction, etc. of the carrier latex particles, a blocking treatment (masking treatment) of the carrier may be performed as necessary by a known method which includes bringing an agent, for example, a protein such as bovine serum albumin (BSA), casein, gelatin, egg albumin, or a salt thereof, a surfactant or fat-free dry milk into contact with the surfaces of the latex particles to thereby coat the particle surfaces with the agent.

(Imidazole)

In the present invention, measurement of an analyte in a sample is performed in the presence of imidazole or an imidazole derivative, or a salt thereof which is allowed to be present or contained in a measurement reaction liquid or a measurement reagent.

Imidazole or imidazole derivative can be any compound having an imidazole skeleton. Examples may include known compounds such as imidazole, 1-methylimidazole, 1-ethylimidazole, 1-propylimidazole, 1-butylimidazole, 1-phenylimidazole, 1-vinylimidazole, 1-allylimidazole, 1-benzyl- 2-methylimidazole, 1-benzyl-2-formylimidazole, 1-benzyl-4-hydroxymethylimidazole, 1-benzyl-5-hydroxymethylimidazole, 1-(2-hydroxyethyl)-imidazole, 1-(2-hydroxyethyl)-2-methylimidazole, 2-methylimidazole, 2-ethylimidazole, 2-propylimidazole, 2-butylimidazole, 2-phenylimidazole, 2-formylimidazole, 2-hydroxymethylimidazole, 2-methyl-1-vinylimidazole, 2-butyl-4-formylimidazole, 2-butyl-4-hydroxymethylimidazole, 2-butyl-4-chloro-5-formylimidazole, 2-hydroxymethyl-1-benzylimidazole, 2-hydroxymethyl-2-methylimidazole, 2-ethyl-4-methylimidazole, 4-butylimidazole, 4-formylimidazole, 4-formyl-1-methylimidazole, 4-formyl-1-tritylimidazole, 5-formyl-1-methylimidazole, 4-formyl-5-methylimidazole, 4-hydroxymethylimidazole hydrochloride, methylimidazole-4-carboxylate, ethylimidazole-4-carboxylate, 1,2-dimethylimidazole, and 1,2,4-trimethylimidazole.

The salt of imidazole or imidazole derivative is a chemically acceptable salt, and includes a potassium salt, a magnesium salt, a lithium salt, a calcium salt, and a zinc salt. Further, the salt of imidazole or imidazole derivative may be a salt selected from the group consisting of adipate, alginate, citrate, aspartate, benzoate, benzene sulfonate, bisulfate, butyrate, camphorate, camphorsulfonate, digluconate, glycerophosphate, hemisulfate, heptanoate, hexanoate, fumarate, sesqui(fumarate), hydrochlorate, dihydrochlorate, trihydrochlorate, hydrobromide, hydroiodide, 2-hydroxyethane sulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, sulfate, bis(tartrate), tartrate, (L)tartrate, bis((L)tartrate), (D)tartrate, bis((L)tartrate), (DL)tartrate, bis((DL)tartrate), mesotartrate, bis(mesotartrate), thiocyanate, phosphate, glutamate, hydrocarbonate, bis((D)tartrate), bis(bromide), bis(sulfate), bis(phosphate), tris(hydrochlorate), p-toluenesulfonate, and undecanoate.

In the present invention, a commercial product can be used as it is as imidazole or an imidazole derivative, or a salt thereof (hereinafter sometimes referred to as imidazole or the like). There is no particular limitation on the concentration of imidazole or the like as long as it does not significantly affect a main reaction, such as an antigen-antibody reaction, in a process step in which an agglutination reaction is measured after mixing a sample and a measurement reagent. However, the lower limit of the concentration may be, for example, 37.5 mM or above, 45 mM or above, 52.5 mM or above, 60 mM or above, 67.5 mM or above, or 75 mM or above. The upper limit of the concentration may be, for example, 750 mM or below, 675 mM or below, 600 mM or below, 525 mM or below, 450 mM or below, 375 mM or below, 300 mM or below, or 225 mM or below.

The concentration of imidazole or the like preferably lies in the range of 37.5 to 750 mM. The concentration also preferably lies in a range as defined by a combination of the aforementioned upper and lower limits, such as the range of 37.5 to 675 mM, 37.5 to 600 mM, 37.5 to 525 mM, 37.5 to 450 mM, 37.5 to 375500 mM, or 37.5 to 300 mM, more preferably in the range of 37.5 to 225 mM, 45 to 225 mM, 52.5 to 225 mM, 60 to 225 mM, or 67.5 to 225 mM, and particularly preferably in the range of 75 to 225 mM.

While there is no problem if the concentration of imidazole or the like exceeds 375 mM, an adequate effect can be achieved at a concentration of not more than 375 mM. A single imidazole species or a plurality of imidazole species may be used as imidazole or the like. In the case of using a plurality of imidazole species, the overall concentration of the imidazole species may preferably lie in the aforementioned range.

The "buffer solution containing imidazole" contained in a measurement reagent according to the present invention may be imidazole buffer solution or a buffer solution other than imidazole buffer solution, containing imidazole or the like. It is also possible to use imidazole buffer solution in combination with a buffer solution other than imidazole buffer solution.

When the measuring method of the present invention is a multi-step method (multi-reagent method) performed in at least two steps (using at least two reagents), the concentration of imidazole or an imidazole derivative, or a salt thereof in a reagent(s) may be determined so that after mixing reagents at a predetermined mixing ratio upon measurement of an analyte, the concentration of imidazole or the like in the resulting measurement reaction liquid will lie in the aforementioned range. In the case of two-step method (two-reagent method), for example, imidazole or the like may be contained in both of a first reagent and a second reagent as long as the concentration of imidazole or the like in a measurement reaction liquid after mixing of the reagents lies in the aforementioned range.

(Contact)

Contact between a sample containing an analyte and latex particles carrying a substance having a specific affinity for the analyte in the presence of imidazole or the like can be effected simply by allowing imidazole or the like to be present in a reaction liquid in which the sample is reacted with the latex particles carrying a substance having a specific affinity for the analyte, and typically can be performed in one of the following manners (1) to (4):

(1) a manner in which after mixing the sample and a buffer solution containing imidazole or the like, the mixture is mixed with a reagent containing the latex particles carrying a substance having a specific affinity for the analyte;

(2) a manner in which the sample, a buffer solution containing imidazole or the like, and a reagent containing the latex particles carrying a substance having a specific affinity for the analyte are mixed simultaneously;

(3) a manner in which after mixing the sample and a reagent containing the latex particles carrying a substance having a specific affinity for the analyte, a buffer solution containing imidazole or the like is added to and mixed with the mixture; and (4) a manner in which after mixing a reagent containing the latex particles carrying a substance having a specific affinity for the analyte and a buffer solution containing imidazole or the like, the sample is added to and mixed with the mixture.

(Reagent for Measurement)

The measurement reagent of the present invention is composed of two or more constituent reagents. At least one constituent reagent contains latex particles carrying a substance having a specific affinity for an analyte. A constituent reagent which is the same as the at least one constituent reagent and/or a constituent reagent which is different from the at least one constituent reagent contains imidazole or the like. The measurement reagent of the present invention is a liquid reagent.

In particular, the measurement reagent of the present invention is preferably of a two-reagent type consisting of a first reagent and a second reagent. For example, the first reagent contains a buffer solution containing imidazole or the like, and the second reagent contains latex particles carrying a substance having a specific affinity for an analyte.

When the measurement reagent of the present invention is of a three-reagent type consisting of a first reagent, a second reagent and a third reagent, in one example, the first reagent contains a buffer solution for extracting an analyte from a diluted sample, the second reagent contains a buffer solution containing imidazole, and the third reagent contains latex particles carrying a substance having a specific affinity for the analyte.

Imidazole or the like may be contained in some or all of the constituent reagents as long as that can exert the effect of reducing a measurement error caused by a blood sample in a mixed-liquid state upon measurement, and does not affect the stability of the constituent reagent(s).

Thus, in the two-reagent type or the three-reagent type, imidazole or the like may be contained in all the constituent reagents or in all those constituent reagents which do not contain latex particles.

The concentration of imidazole or the like in each constituent reagent may differ depending on the type of the reagent; however, imidazole or the like should preferably be contained in each constituent reagent at such a concentration as to be capable of adjusting the final concentration of imidazole or the like to not less than 37.5 mM and not more than 375 mM in a state of reagent-sample mixture upon measurement.

(Reagent Kit)

The reagent kit of the present invention is characterized in that it includes at least the following elements (1) and (2):

(1) a first reagent containing a buffer solution containing imidazole or the like; and (2) a second reagent containing latex particles carrying a substance having a specific affinity for an analyte.

The concentration of imidazole or the like in the buffer solution may differ depending on the type of the reagent; however, imidazole or the like should preferably be contained in the buffer solution at such a concentration as to be capable of adjusting the final concentration of imidazole or the like to not less than 37.5 mM and not more than 375 mM in a state of reagent-sample mixture upon measurement. For example, when the first reagent and the second reagent are used at a ratio of 3:1, and a sample is used in a very small amount, the concentration of imidazole or the like in the buffer solution as the first reagent is preferably not less than 50 mM and not more than 500 mM.

Besides the above measurement reagents, the reagent kit of the present invention can include an instruction leaflet, a sampling tool(s) (a sampling pipette, a syringe, a cotton swab, a filter, etc.), a sample diluent, and a sample extraction liquid.

(Measurement Error-Reducing Agent)

The measurement error-reducing agent of the present invention is an agent for reducing a measurement error caused by a blood sample in a latex agglutination immunoassay, and contains at least imidazole or the like as an active ingredient. The reagent containing imidazole or the like in the aforementioned measurement reagent can be used as it is.

(Homogeneous Method)

As used herein, a homogeneous method refers to a measuring method which specifically detects, without performing B/F (bond/free) separation, a reaction which is caused by an analyte to progress in a mixed solution (reaction liquid) containing a sample and a reagent liquid, and which stands in contrast to a heterogeneous measuring method which completely cleans and removes, by a B/F separation operation, an extra component that has not been involved in a measurement reaction, and then causes to progress and detects the main reaction. Thus, "the latex agglutination immunoassay is based on a homogeneous method", as used herein, means that in the following typical process steps (1) to (3), the step (3) is "a step of measuring an agglutination reaction between an analyte and latex particles without performing a cleaning or separation step during or after the step (2):

(1) a step of bringing a sample and imidazole or the like into contact with each other in a liquid phase;

(2) a step of adding latex particles carrying a substance having a specific affinity for an analyte to the liquid phase after the step (1); and (3) a step of measuring an agglutination reaction between the analyte and the latex particles after the step (2).

(Other Reagent Components)

The reagent of the present invention may contain a polymer such as polyethylene glycol, polyvinyl pyrrolidone or a phospholipid polymer as a component for reinforcing the formation of agglutination of insoluble carrier particles. The reagent of the present invention may also contain, as a component for controlling the formation of agglutination of carrier particles, a commonly-used material such as a protein, an amino acid, a saccharide, a metal salt, a surfactant, a reducing material, a chaotropic material, etc., which may be used singly or in a combination of two or more.

EXAMPLES

The following examples illustrate the present invention in greater detail and are not to be construed as limiting the scope of the invention.

[Test Example 1] Confirmation of the Measurement Error-Reduction Effect Produced by the Addition of Imidazole According to the Present Invention The influence of lipid in a blood sample on a measurement error was confirmed. Further, a study was made of the effect of the type of a buffer solution and the addition of imidazole or the like on a reduction of measurement error.

1. Reagent (1) First Reagent

A first reagent contained the following components (The concentrations are those in the reagent. The same applies hereinafter.):

A buffer shown in Table 1
500 mM NaCl
1.0% BSA
0.05% Proclin300

(2) Second Reagent

A second reagent was prepared by mixing the following two types of antibody-sensitized latex particle solutions in equal amount, and diluting the mixture with a 5 mM MOPS buffer solution (pH 7.0) so that the absorbance at a wavelength of 600 nm became 5.0 Abs.

(i) Antibody 92212-Sensitized Latex Particle Solution

To a 1.0% solution of latex particles having an average particle diameter of 0.3 μm (5 mM Tris buffer solution (hereinafter referred to as Tris-HCl or simply as Tris) (pH 8.5), an equal amount of an antibody 92212 solution, diluted to 0.36 mg/mL with 5 mM Tris-HCl (pH 8.5), was added, and the mixture was stirred at 4° C. for 2 hours. Thereafter, an equal amount of 5 mM Tris-HCl (pH 8.5) containing 0.5% BSA was added, and the mixture was stirred at 4° C. for 1 hour to prepare an antibody 92212-sensitized latex particle solution.

(ii) Antibody 92204R-Sensitized Latex Particle Solution

Using latex particles having an average particle diameter of 0.3 an antibody 92204R-sensitized latex particle solution was prepared in the same manner as described in (i) above.

2. Test Sample

Serum A (pooled serum A) which was randomly sampled and mixed

3. Sample Preparation Method (The concentrations of Intralipos are those in the sample before mixing with the reagents. The same applies hereinafter.)

One part of an intravenous fat emulsion (Intralipos infusion solution 10% (Otsuka Pharmaceutical Co., Ltd.)) which had been mixed with an equal amount of physiological saline (Otsuka Pharmaceutical Co., Ltd.), was added to 9 parts of the test sample to prepare a 0.5% Intralipos sample.

One part of physiological saline was added to 9 parts of the test sample to prepare a 0% Intralipos sample.

One part of the 0.5% Intralipos sample was added to 4 parts of the test sample to prepare a 0.1% Intralipos sample.

4. Measuring Method

Using the first reagent in combination with the second reagent, the concentration of soluble interleukin-2 receptor in a sample containing intravenous fat emulsion was measured by means of a Hitachi 7180 autoanalyzer. Specifically, 150 μL of the first reagent was added to 5 μL of a sample, and the mixture was stirred at 37° C. for 5 minutes. Thereafter, 50 μL of the second reagent was added to the mixture, and the mixture was stirred. The change in absorbance associated with the formation of agglutination was measured at a dominant wavelength of 570 nm and a complementary wavelength of 800 nm for 5 minutes thereafter. The concentration of soluble interleukin-2 receptor was calculated by applying the measured change in absorbance to a calibration curve obtained by measuring a standard substance at known concentrations (common to Test Examples 1 to 3).

Relative measurement values for Intralipos samples at different concentrations were calculated using the measurement value for the 0% Intralipos sample as 100% (common to Test Examples 1 and 2).

5. Measurement Conditions

The following are parameter conditions of the Hitachi 7180 autoanalyzer:

(1) Liquid amount: sample-first reagent-second reagent; 5 μL-150 μL-50 μL (2) Analysis method: 2 point end method (photometric points 19-34)

(3) Measurement wavelength: dominant wavelength 570 nm/complementary wavelength 800 nm (4) Calibration: spline 6. Measurement Results When a measurement value for the 0.1% Intralipos sample, relative to the measurement value for the 0% Intralipos sample which is taken as 100%, is less than 85% or more than 115%, the value was determined to be affected by the coexistence of Intralipos. The results are shown in Table 1.

TABLE 1

| Sample | Comp. Ex. 1 | Comp. Ex. 2 | Example 1 | Example 2 | Example 3 |
| --- | --- | --- | --- | --- | --- |
| | | | Buffer | | |
| | 100 mM Tris | 100 mM HEPES | 100 mM Imidazole Buffer | 100 mM Tris + 100 mM Imidazole Buffer | 100 mM HEPES + 100 mM Imidazole Buffer |
| 0% Intralipos Sample | 100.0% | 100.0% | 100.0% | 100.0% | 100.0% |

TABLE 1-continued

| Sample | Comp. Ex. 1 | Comp. Ex. 2 | Example 1 | Example 2 | Example 3 |
| --- | --- | --- | --- | --- | --- |
| | | | Buffer | | |
| | 100 mM Tris | 100 mM HEPES | 100 mM Imidazole Buffer | 100 mM Tris + 100 mM Imidazole Buffer | 100 mM HEPES + 100 mM Imidazole Buffer |
| 0.1% Intralipos Sample | 135.1% | 152.6% | 109.1% | 103.7% | 105.9% |

7. Discussion

When only Tris or HEPES was used as a buffer in the first reagent, the measurement value was affected by the coexistence of Intralipos. In contrast, when only the imidazole buffer was used, or the imidazole buffer was used in combination with Tris or HEPES, the measurement value was not affected by the coexistence of Intralipos.

[Test Example 2] Relationship Between the Concentration of Imidazole and the Effect of Reducing Measurement Error The concentration of imidazole in the immunoagglutination-reaction liquid was varied to examine the relationship between the concentration of imidazole and the effect of reducing a measurement error.

1. Reagent (1) First Reagent

The same first reagent as that of Test Example 1 was used except for replacing the buffer solutions shown in Table 1 with the buffer solutions shown in Table 2.

(2) Second Reagent

The same second reagent as that of Test Example 1 was used.

2. Test Sample (1) Serum B (pooled serum B) which was randomly sampled and mixed (2) Serum C (pooled serum C) which was randomly sampled and mixed (3) Serum D (pooled serum D) which was randomly sampled and mixed 3. Sample Preparation Method A 0.5% Intralipos sample, a 0% Intralipos sample and a 0.1% Intralipos sample were prepared in the same manner as in Test Example 1. A 0.05% Intralipos sample was prepared by adding one part of the 0.5% Intralipos sample to nine parts of the test sample.

4. Measuring Method and 5. Measurement Conditions

The same as those of Test Example 1.

6. Measurement Results

When a measurement value for the 0.05% Intralipos sample or the 0.1% Intralipos sample, relative to the measurement value for the 0% Intralipos sample which is taken as 100%, is not less than 85% and not more than 115%, the value was determined to be not affected (+) by the coexistence of Intralipos.

+++ indicates that no influence of Intralipos was observed for any of the pooled serums B to D, ++ indicates that no influence of Intralipos was observed for any two of the pooled serums B to D, and + indicates that no influence of Intralipos was observed for any one of the pooled serums B to D. The results are shown in Table 2.

TABLE 2

| Sample | Example 4<br>50 mM Imidazole Buffer | Example 5 Buffer<br>100 mM imidazole Buffer | Example 6<br>300 mM Imidazole Buffer |
|---|---|---|---|
| 0% Intralipos Sample | +++ | +++ | +++ |
| 0.05% Intralipos Sample | +++ | +++ | +++ |
| 0.1% Intralipos Sample | ++ | +++ | +++ |

7. Discussion

It was found that Imidazole, when used at a concentration of 50 mM to 300 mM in the imidazole buffer, can avoid the influence of Intralipos.

[Test Example 3] Examination of the Cause of Measurement Error

In order to determine whether a measurement error is caused only by a blood sample containing lipid or by a reagent containing latex, an experiment was conducted using a reagent containing no latex as the second reagent.

1. Reagent
(1) First Reagent

The same first reagent as that of Test Example 1 was used except for replacing the buffer solutions shown in Table 1 with 100 mM Tris (pH 7.0).

(2) Second Reagent
Physiological saline
2. Test Sample

The same pooled serum B, pooled serum C and pooled serum D as those of Test Example 2.

3. Sample Preparation Method
The same as that of Test Example 2.
4. Measuring Method and 5. Measurement Conditions
The same as those of Test Example 1.
6. Measurement Results and Discussion The measured absorbance was 0 to 1.2 mAbs. An increase in absorbance, which is dependent on the concentration of Intralipos, was not observed. This implies that a measurement value is affected not by the turbidity of a blood sample, caused by the addition of Intralipos, but by the nonspecific agglutination of latex particles caused by contact with a blood sample containing Intralipos.

INDUSTRIAL APPLICABILITY

There is provided a method which, in a latex agglutination immunoassay, can reduce a measurement error caused by a blood sample, and which includes a step of bringing a blood sample into contact with latex particles carrying a substance having a specific affinity for an analyte in a liquid phase in the presence of imidazole or an imidazole derivative, or a salt thereof. The method of the present invention makes it possible to accurately perform a measurement, by a latex agglutination immunoassay, even for a lipid-rich sample e.g. from a patient with hyperlipidemia.

The invention claimed is:

1. A method for measuring an analyte in a chylous plasma or chylous serum by a latex agglutination immunoassay, comprising the following steps:
   (1) bringing a chylous plasma or chylous serum containing chyle into contact with imidazole or an imidazole derivative, or a salt thereof in a liquid phase;
   (2) adding latex particles carrying a substance having a specific affinity for the analyte to the liquid phase sequentially after the step (1); and
   (3) measuring an agglutination reaction between the analyte and the latex particles after the step (2), without performing a cleaning or separation step during or after the step (2),
   wherein the concentration of imidazole or an imidazole derivative, or a salt thereof in the step (3) of measuring the agglutination reaction of the latex particles is not less than 100 mM and not more than 375 mM.

2. A method for measuring an analyte in a chylous plasma or chylous serum by a latex agglutination immunoassay, comprising the following steps:
   (1) bringing a chylous plasma or chylous serum into contact with imidazole or an imidazole derivative, or a salt thereof in a liquid phase;
   (2) adding latex particles carrying a substance having a specific affinity for the analyte to the liquid phase after the step (1); and
   (3) measuring an agglutination reaction between the analyte and the latex particles after the step (2), without performing a cleaning or separation step prior to the measurement step (3),
   wherein the concentration of imidazole or an imidazole derivative, or a salt thereof in the step (3) of measuring the agglutination reaction of the latex particles is not less than 100 mM and not more than 375 mM.

3. The method according to claim 1, wherein said step of bringing a chylous plasma or chylous serum into contact with imidazole or an imidazole derivative, or a salt thereof in a liquid phase is a step of adding a first reagent to a chylous plasma or chylous serum, thereby producing a first mixture, wherein said first reagent contains a buffer solution containing imidazole or an imidazole derivative, or a salt thereof; and
wherein said step of adding latex particles carrying a substance having a specific affinity for the analyte to the liquid phase is a step of adding a second reagent to the first mixture, wherein said second reagent contains latex particles carrying a substance having a specific affinity for the analyte.

4. The method according to claim 3, wherein said first reagent is a buffer solution containing imidazole or an imidazole derivative, or a salt thereof.

5. The method according to claim 4, wherein said second reagent is a suspension of latex particles carrying a substance having a specific affinity for the analyte.

6. The method according to claim 5, wherein the step of measuring an agglutination reaction between the analyte and the latex particles is a step of measuring an agglutination reaction between an analyte and latex particles without performing a cleaning or separation step during or after the step of adding a suspension of latex particles carrying a substance having a specific affinity for the analyte to the first mixture.

7. The method according to claim 1, wherein said imidazole or imidazole derivative or salt thereof is selected from the group consisting of imidazole, 1-methylimidazole, 1-ethylimidazole, 1-propylimidazole, 1-butylimidazole, 1-phenylimidazole, 1-vinylimidazole, 1-allylimidazole, 1-benzyl-2-methylimidazole, 1-benzyl-2-formylimidazole, 1-benzyl-4-hydroxymethylimidazole, 1-benzyl-5-hydroxymethylimidazole, 1-(2-hydroxyethyl)-imidazole, 1-(2-hydroxyethyl)-2-methylimidazole, 2-methylimidazole, 2-ethylimidazole, 2-propylimidazole, 2-butylimidazole, 2-phenylimidazole, 2-formylimidazole, 2-hydroxymethylimidazole, 2-methyl-1-vinylimidazole, 2-butyl-4-formylimidazole, 2-butyl-4-hydroxymethylimidazole, 2-butyl-4-chloro-5-formylimidazole, 2-hydroxymethyl-1-benzylimidazole, 2-hydroxymethyl-2-methylimidazole, 2-ethyl-4-methylimidazole, 4-butylimidazole, 4-formylimidazole, 4-formyl-1-methylimidazole, 4-formyl-1-tritylimidazole, 5-formyl-1-methylimidazole, 4-formyl-5-methylimidazole, 4-hydroxymethylimidazole hydrochloride, methylimidazole-4-carboxylate, ethylimidazole-4-carboxylate, 1,2-dimethylimidazole, 1,2,4-trimethylimidazole and a salt of any of said imidazole or imidazole derivatives.

8. The method according to claim 6, wherein said imidazole or imidazole derivative or salt thereof is selected from the group consisting of imidazole, 1-methylimidazole, 1-ethylimidazole, 1-propylimidazole, 1-butylimidazole, 1-phenylimidazole, 1-vinylimidazole, 1-allylimidazole, 1-benzyl-2-methylimidazole, 1-benzyl-2-formylimidazole, 1-benzyl-4-hydroxymethylimidazole, 1-benzyl-5-hydroxymethylimidazole, 1-(2-hydroxyethyl)-imidazole, 1-(2-hydroxyethyl)-2-methylimidazole, 2-methylimidazole, 2-ethylimidazole, 2-propylimidazole, 2-butylimidazole, 2-phenylimidazole, 2-formylimidazole, 2-hydroxymethylimidazole, 2-methyl-1-vinylimidazole, 2-butyl-4-formylimidazole, 2-butyl-4-hydroxymethylimidazole, 2-butyl-4-chloro-5-formylimidazole, 2-hydroxymethyl-1-benzylimidazole, 2-hydroxymethyl-2-methylimidazole, 2-ethyl-4-methylimidazole, 4-butylimidazole, 4-formylimidazole, 4-formyl-1-methylimidazole, 4-formyl-1-tritylimidazole, 5-formyl-1-methylimidazole, 4-formyl-5-methylimidazole, 4-hydroxymethylimidazole hydrochloride, methylimidazole-4-carboxylate, ethylimidazole-4-carboxylate, 1,2-dimethylimidazole, 1,2,4-trimethylimidazole and a salt of any of said imidazole or imidazole derivatives.

9. The method according to claim 2, wherein step (1) comprises bringing the chylous plasma or chylous serum into contact with a buffer solution containing imidazole or an imidazole derivative, or a salt thereof.

10. The method according to claim 9, wherein the latex particles are added in the form of a suspension of latex particles carrying a substance having a specific affinity for the analyte.

11. The method according to claim 10, wherein the step of measuring an agglutination reaction between the analyte and the latex particles is a step of measuring an agglutination reaction between an analyte and latex particles without performing a cleaning or separation step during or after the step of adding a suspension of latex particles carrying a substance having a specific affinity for the analyte to the first mixture.

12. The method according to claim 2, wherein said imidazole or imidazole derivative or salt thereof is selected from the group consisting of imidazole, 1-methylimidazole, 1-ethylimidazole, 1-propylimidazole, 1-butylimidazole, 1-phenylimidazole, 1-vinylimidazole, 1-allylimidazole, 1-benzyl-2-methylimidazole, 1-benzyl-2-formylimidazole, 1-benzyl-4-hydroxymethylimidazole, 1-benzyl-5-hydroxymethylimidazole, 1-(2-hydroxyethyl)-imidazole, 1-(2-hydroxyethyl)-2-methylimidazole, 2-methylimidazole, 2-ethylimidazole, 2-propylimidazole, 2-butylimidazole, 2-phenylimidazole, 2-formylimidazole, 2-hydroxymethylimidazole, 2-methyl-1-vinylimidazole, 2-butyl-4-formylimidazole, 2-butyl-4-hydroxymethylimidazole, 2-butyl-4-chloro-5-formylimidazole, 2-hydroxymethyl-1-benzylimidazole, 2-hydroxymethyl-2-methylimidazole, 2-ethyl-4-methylimidazole, 4-butylimidazole, 4-formylimidazole, 4-formyl-1-methylimidazole, 4-formyl-1-tritylimidazole, 5-formyl-1-methylimidazole, 4-formyl-5-methylimidazole, 4-hydroxymethylimidazole hydrochloride, methylimidazole-4-carboxylate, ethylimidazole-4-carboxylate, 1,2-dimethylimidazole, 1,2,4-trimethylimidazole and a salt of any of said imidazole or imidazole derivatives.

13. The method according to claim 11, wherein said imidazole or imidazole derivative or salt thereof is selected from the group consisting of imidazole, 1-methylimidazole, 1-ethylimidazole, 1-propylimidazole, 1-butylimidazole, 1-phenylimidazole, 1-vinylimidazole, 1-allylimidazole, 1-benzyl-2-methylimidazole, 1-benzyl-2-formylimidazole, 1-benzyl-4-hydroxymethylimidazole, 1-benzyl-5-hydroxymethylimidazole, 1-(2-hydroxyethyl)-imidazole, 1-(2-hydroxyethyl)-2-methylimidazole, 2-methylimidazole, 2-ethylimidazole, 2-propylimidazole, 2-butylimidazole, 2-phenylimidazole, 2-formylimidazole, 2-hydroxymethylimidazole, 2-methyl-1-vinylimidazole, 2-butyl-4-formylimidazole, 2-butyl-4-hydroxymethylimidazole, 2-butyl-4-chloro-5-formylimidazole, 2-hydroxymethyl-1-benzylimidazole, 2-hydroxymethyl-2-methylimidazole, 2-ethyl-4-methylimidazole, 4-butylimidazole, 4-formylimidazole, 4-formyl-1-methylimidazole, 4-formyl-1-tritylimidazole, 5-formyl-1-methylimidazole, 4-formyl-5-methylimidazole, 4-hydroxymethylimidazole hydrochloride, methylimidazole-4-carboxylate, ethylimidazole-4-carboxylate, 1,2-dimethylimidazole, 1,2,4-trimethylimidazole and a salt of any of said imidazole or imidazole derivatives.

* * * * *